United States Patent
Hao et al.

(10) Patent No.: US 10,175,180 B2
(45) Date of Patent: Jan. 8, 2019

(54) MEASUREMENT TECHNIQUE FOR THIN-FILM CHARACTERIZATION

(71) Applicant: The Secretary of State For Business, Innovation & Skills, London (GB)

(72) Inventors: Ling Hao, Middlesex (GB); John Charles Gallop, Middlesex (GB)

(73) Assignee: NPL Management Limited (GB)

(*) Notice: Subject to any disclaimer, the term of this patent is extended or adjusted under 35 U.S.C. 154(b) by 184 days.

(21) Appl. No.: 15/328,703

(22) PCT Filed: Jul. 24, 2015

(86) PCT No.: PCT/GB2015/052153
§ 371 (c)(1),
(2) Date: Jan. 24, 2017

(87) PCT Pub. No.: WO2016/012809
PCT Pub. Date: Jan. 28, 2016

(65) Prior Publication Data
US 2017/0212060 A1     Jul. 27, 2017

(30) Foreign Application Priority Data
Jul. 25, 2014 (GB) .................................. 1413237.7

(51) Int. Cl.
*G01N 22/00* (2006.01)
(52) U.S. Cl.
CPC .................................. *G01N 22/00* (2013.01)
(58) Field of Classification Search
CPC .................................................... G01N 22/00
(Continued)

(56) References Cited

U.S. PATENT DOCUMENTS 6,005,916 A * 12/1999 Johnson .................. A61B 5/05
378/87
2007/0091008 A1* 4/2007 Mortazawi ............... H01Q 3/26
343/864

OTHER PUBLICATIONS

Hao et al., "Non-contact method for measurement of the microwave conductivity of graphene", *Applied Physics Letters*, 2013, vol. 103, No. 12, p. 123103.

(Continued)

*Primary Examiner* — Melissa Koval
*Assistant Examiner* — Trung Nguyen
(74) *Attorney, Agent, or Firm* — Joseph T. Leone, Esq.; DeWitt Ross & Stevens S.C.

(57) ABSTRACT

A measurement device comprises a high permittivity dielectric resonator (10) with a low microwave loss tangent and having at least a first symmetry axis (z-i); an electrically conductive resonance chamber (100) containing and geometrically similar to the resonator (10) and having a second symmetry axis (z2) coincident with the first symmetry axis (z-i); the resonance chamber (100) having a plurality of similar ports (104) orthogonal to the first symmetry axis (z-i), each such port (104) having a microwave antenna (114), either to inject microwaves into the resonance chamber, thereby to excite an electric field in the resonator, or to receive microwaves from the resonance chamber; and a comparator circuit (200, 300, 400, 500, 600, 700, 800) connected to a first one (P1) of the plurality of ports (104) to inject microwaves into the resonance chamber and to another (P2, P3) of the plurality of ports (104) to receive microwaves from the resonance chamber; wherein the measurement device further comprises an electrically conductive tuning screw (106) in electrical contact with the resonance chamber (100), the tuning screw being at least partially positionable in the electric field thereby excited in the resonator; and a source of magnetism (18) to apply a (Continued)

magnetic field to a sample brought into proximity with a top surface (12) of the resonator (10) substantially parallel or anti-parallel to the first symmetry axis (z-i); and wherein one (P3) of the other of the plurality of ports (104) to receive microwaves from the resonance chamber (100) is orthogonal to the first one (P1) of the plurality of ports (104) to inject microwaves into the resonance chamber. Such a measurement device may be used to measure both the conductivity or sheet resistance of a thin film (30), as well as the carrier mobility of the thin film, without contacting the resonator (10) with either the thin film or a substrate (20) on which the thin film is formed.

21 Claims, 13 Drawing Sheets

(58) Field of Classification Search
USPC ............ 427/123, 129, 271, 384, 255.6, 250, 427/535–539; 324/600, 633–708, 71.1, 324/300–322, 263, 76.11, 76.49, 76.51
See application file for complete search history.

(56) References Cited

OTHER PUBLICATIONS

Krupka, Jerry, "Topical Review; contactless methods of conductivity and sheet resistance measurement for semiconductors, conductors and superconductors; Contactless methods of conductivity and sheet resistance measurement for semiconductors, conductor", *Measurement Science and Technology*, 2013, col. 24, Sections 5 and 6.
Sayed et al., "Microwave Hall measurement techniques on low mobility semiconductors and insulators. II. Experimental procedures", *Rev. Sci. Instrum.*, Aug. 1975, vol. 46, No. 8, pp. 1080-1085.

* cited by examiner

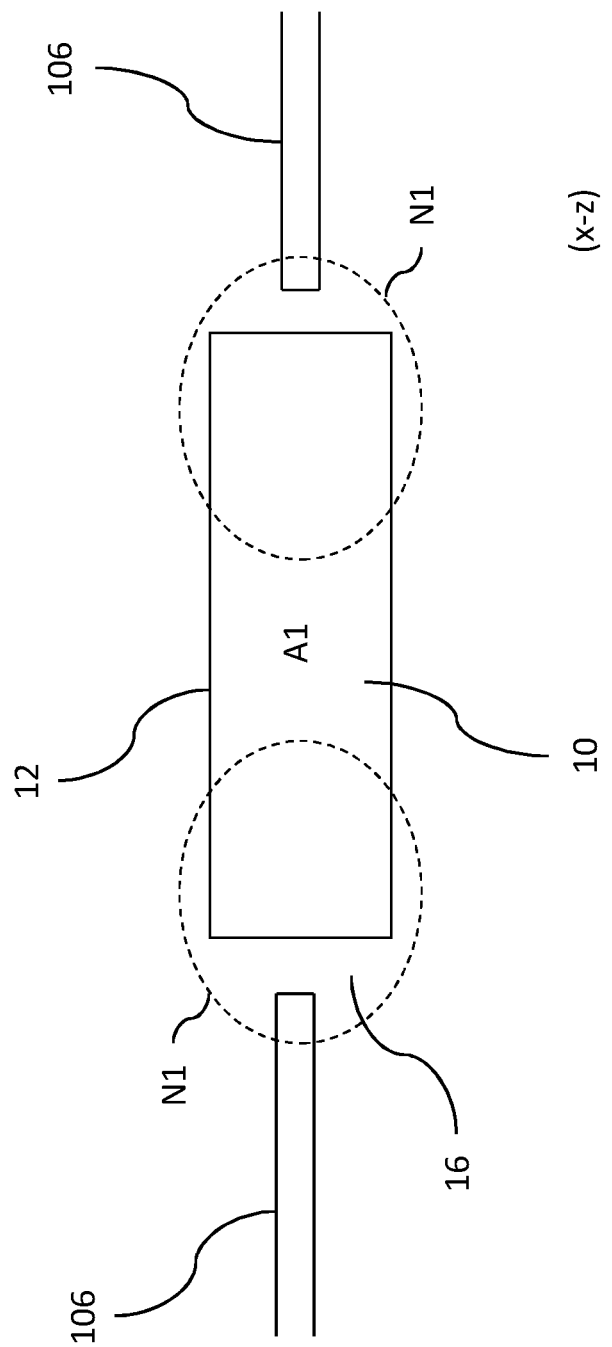

MEASUREMENT TECHNIQUE FOR THIN-FILM CHARACTERIZATION

FIELD OF THE INVENTION

The present invention concerns measurement techniques for characterizing thin films, and in particular for determining the carrier mobility of a thin film, as well as the conductivity or equivalently, the sheet resistance of a thin film.

BACKGROUND ART

The inventors have previously described a technique for measuring the conductivity and sheet resistance of thin-film samples of graphite comprising monolayers and very few layers of graphene in their paper "Non-contact method for measurement of the microwave conductivity of graphene" in Applied Physics Letters, Vol. 103, pp. 123103-1-123103-4 (2013). This technique uses a high Q-factor dielectric resonator, made of a single crystal of a high permittivity material with a low microwave loss tangent, such as sapphire, which is excited by microwaves in a conducting chamber, to measure the conductivity of such thin-film samples in a non-contacting manner. As described at the end of that paper, the present inventors indicated that it would also be desirable to find a technique for measuring the carrier mobility of thin-film samples in a similarly non-contacting way.

Until now, the carrier mobility of thin-film samples such as monolayers and very few layers of graphene has been measured using a contacting method, which comprises patterning a thin-film sample into a Hall bar device on a substrate, such as an oxidised silicon wafer, and attaching electrodes to the sample in order to determine the carrier mobility of the sample from field-effect and magneto resistance measurements, as described, for example, in "Electrical Field Effect in Atomically Thin Carbon Films" by K. S. Novoselov, A. K. Geim et al. in Science, Vol. 306, pp. 666-669 (22 Oct. 2004) and in "Two-dimensional atomic crystals" by K. S. Novoselov et al. in Proceedings Nat. Acad. Sci., Vol. 102, no. 30, pp. 10451-10453 (26 Jul. 2005).

Such techniques can exhibit the disadvantages of being time-consuming and inefficient to prepare the samples as Hall bar devices and destructive of the thin-film sample to be measured.

On the other hand, it is also known to measure the carrier mobility of a semiconductor sample in a non-contacting way by placing such a sample in a rectangular cavity resonator and injecting the cavity with microwaves to excite the sample into an orthogonal mode in the presence of a static magnetic field. However, this technique has the disadvantage that although the sample is not destroyed by such a technique, it is difficult to characterize the Hall coefficient of the sample and its mobility with any accuracy. This is for several reasons. Firstly, it is difficult to achieve a high Q-factor in the cavity. Secondly, only samples of very small volume can be used and usually the shape and position of the sample within the cavity are critical, since the complicated geometry of the rectangular cavity relative to the sample makes calculation of the coupling between the sample and the cavity problematic. Furthermore, there is a direct effect of the magnetic field on the conducting walls of the cavity, which arises from the small but finite Hall coefficient of the metal from which the cavity is made. This technique is therefore not favoured.

Reference is also made to the article Measurement Science and Technology, Vol. 24, 2013, Jerzy Krupka, "Topical Review; Contactless methods of conductivity and sheet resistance measurement for semiconductors, conductors and superconductors; Contactless methods of conductivity and sheet resistance measurement for semiconductors, conductor". This discusses microwave techniques in Section 5 and microwave measurements of charge carrier mobility and charge carrier concentration in Section 6.

SUMMARY OF THE INVENTION

According to a first aspect of the present invention, there is provided a measurement device comprising a high permittivity dielectric resonator with a low microwave loss tangent and having at least a first symmetry axis; an electrically conductive resonance chamber containing and geometrically similar to the resonator and having a second symmetry axis coincident with the first symmetry axis; the resonance chamber having a plurality of similar ports orthogonal to the first symmetry axis, each such port having a microwave antenna, either to inject microwaves into the resonance chamber, thereby to excite an electric field in the resonator, or to receive microwaves from the resonance chamber; and a comparator circuit connected to a first one of the plurality of ports to inject microwaves into the resonance chamber and to another of the plurality of ports to receive microwaves from the resonance chamber; wherein the measurement device further comprises an electrically conductive tuning screw in electrical contact with the resonance chamber, the tuning screw being at least partially positionable in the electric field thereby excited in the resonator; and a source of magnetism to apply a magnetic field to a sample brought into proximity with a top surface of the resonator substantially parallel or anti-parallel to the first symmetry axis; and wherein one of the other of the plurality of ports to receive microwaves from the resonance chamber is orthogonal to the first one of the plurality of ports to inject microwaves into the resonance chamber.

In preferred embodiments, the resonator is a right circular cylinder of rotation about the first symmetry axis ($z_1$).

The resonance chamber preferably comprises an opening, allowing a sample to be introduced to a near-field region of the electric field excited in the resonator. The near-field region of the electric field excited in the resonator preferably extends beyond the opening of the resonance chamber.

The walls of the resonance chamber may be made of a material selected from the group consisting of copper and aluminium.

In a preferred embodiment, a second one of the other of the plurality of ports to receive microwaves from the resonance chamber is opposite the first one of the plurality of ports to inject microwaves into the resonance chamber, with the resonator located therebetween. Thus this second port is a so-called "in-line" port. A third one of the other of the plurality of ports to receive microwaves from the resonance chamber is opposite the one of the other of the plurality of ports to receive microwaves from the resonance chamber, with the resonator located therebetween. Thus this third port is another orthogonal port.

The tuning element is preferably a tuning screw mounted to the resonance chamber coplanar with the plurality of ports, the tuning screw being mounted about the first symmetry axis ($z_1$) at an angle of 45 degrees to a respective one of the plurality of ports, and being at least partially positionable in the electric field of the resonator by being turnable on a screw thread.

The microwave antenna may be a straight mode or wire loop antenna.

The comparator circuit may comprise a vector network analyser with channels respectively connected to the first one of the plurality of ports to inject microwaves into the resonance chamber and to the other of the plurality of ports to receive microwaves from the resonance chamber.

The comparator circuit may include a loop oscillator comprising: a fast microwave switch connected to the other of the plurality of ports to receive microwaves from the resonance chamber; a phase shifter connected to the fast microwave switch; a tunable band pass filter connected to the phase shifter; and a microwave amplifier connected to the band pass filter and to the first one of the plurality of ports to inject microwaves into the resonance chamber; the loop oscillator being connected to at least one of a counter and an oscilloscope.

According to a second aspect of the present invention, there is provided a method of measuring the carrier mobility of a thin film, comprising: providing a measuring device according to the first aspect of the invention; injecting microwaves into the resonance chamber via the first one of the plurality of ports to excite an electric field in the resonator; receiving microwaves from the resonance chamber via the one of the other of the plurality of ports; adjusting a position of the tuning element in the electric field thereby excited in the resonator until the microwaves received from the resonance chamber via the one of the other of the plurality of ports show that a first mode of the electric field thereby excited in the resonator is degenerate with a second mode thereof orthogonal to the first mode; introducing a substrate having the thin film formed thereon into the near-field region of the electric field; receiving microwaves again from the resonance chamber via the one of the other of the plurality of ports; measuring a first peak output power of the microwaves received via the one of the other of the plurality of ports; whilst applying a magnetic field to the substrate having the thin film formed thereon substantially parallel or anti-parallel to the first symmetry axis, receiving microwaves again from the resonance chamber via the one of the other of the plurality of ports; measuring a second peak output power of the microwaves received via the one of the other of the plurality of ports; and comparing the first and second peak output powers with each other to derive the carrier mobility of the thin film.

The teachings herein are able to provide for measurement of carrier mobility of a thin-film sample in a non-contacting way. They can also provide a measuring device for carrying out such a method of measuring the carrier mobility of a thin film, as well as a method of measuring the conductivity or equivalently, the sheet resistance of a thin film using such an alternative measuring device, which can, if desired, again be used in a non-contacting way.

The carrier mobility of the thin film is proportional to the ratio of the first and second peak output powers and the constant of proportionality may be determined by calibration against a measurement of the carrier mobility conducted on a similar sample using a conventional technique.

According to a third aspect of the present invention, there is provided a method of measuring the conductivity or sheet resistance of a thin film, comprising providing a measuring device according to the first aspect of the invention; injecting microwaves into the resonance chamber via the first one of the plurality of ports to excite an electric field in the resonator; introducing a bare substrate into a near-field region of the electric field thereby excited in the resonator; receiving microwaves from the resonance chamber via the second one of the other of the plurality of ports; measuring a first resonant frequency and a first line width of the peak output power of the microwaves received via the second one of the other of the plurality of ports; removing the bare substrate from the near-field region of the electric field excited in the resonator; introducing a like substrate having the thin film formed thereon into the same location in the near-field region of the electric field excited in the resonator as was previously occupied by the bare substrate; receiving microwaves from the resonance chamber via the second one of the other of the plurality of ports; measuring a second resonant frequency and a second line width of the peak output power of the microwaves received via the second one of the other of the plurality of ports; and comparing the first and second resonant frequencies and the first and second line widths with each other to derive the conductivity or sheet resistance of the thin film.

The method of measuring the conductivity or sheet resistance may use either an orthogonal port or an in-line port depending on the particular microwave mode selected for this operation.

The mathematical technique for deriving the conductivity or sheet resistance of the thin film from the first and second resonant frequencies and the first and second line widths is described in the inventors' paper "Non-contact method for measurement of the microwave conductivity of graphene" in Applied Physics Letters, Vol. 103, pp. 123103-1-123103-4 (2013), referred to above. The substitutional technique for measuring the first and second resonant frequencies and the first and second line widths of a thin film in this way obviates the need for finite element modelling of the microwave fields, which would prove difficult in the case of a material such as graphene, where the scale mismatch between the smallest and largest features of a graphene sample are of the order of $10^6$ or more.

The preferred embodiments have the advantage that since the thin film is coupled to a dielectric resonator, there is no first-order contribution from the resonator conductivity, which to all intents and purposes is zero, although there may be a small second-order contribution from the very weak coupling between the resonator and the resonance chamber. However, this second-order contribution may be minimized by making sure that the resonance chamber is sufficiently large to lie outside the electric field excited in the resonator. On the other hand, the present invention also has the advantage that the top surface of the resonator may be made sufficiently large to characterize the properties of an equally large thin film sample, thereby making calculation and calibration simpler and more accurate, even though the total volume of the thin film sample remains extremely small. A most significant advantage of the invention, however, is that it may be used to measure both the conductivity or sheet resistance of the thin film, and the carrier mobility of the thin film, without contacting the resonator with either the thin film or a substrate on which the thin film is formed.

Preferably, the resonator is made of a material selected from the group consisting of sapphire ($Al_2O_3$), lanthanum aluminate ($LaAlO_3$), rutile ($TiO_2$), strontium titanate ($SrTiO_3$) and magnesium oxide (MgO), which are all materials having a high permittivity and a low microwave loss tangent, when grown as a single crystal. Preferably, the relative permittivity of the resonator is greater than 8 and the microwave loss tangent of the resonator is less than $10^{-4}$.

It is also preferred that the electric field excited in the resonator should be a $TE_{nmp}$ mode with n>0. Of these, a $TE_{110}$ mode is preferred, although higher order modes may also be used.

The comparator circuit may comprise a vector network analyser (VNA) with channels respectively connected to the first one of the plurality of ports used to inject microwaves into the resonance chamber and to another of the plurality of ports used to receive microwaves from the resonance chamber. This allows either the conductivity or sheet resistance or the carrier mobility of a thin film sample to be derived in the frequency domain. In an alternative embodiment, the comparator circuit may include a loop oscillator comprising a fast microwave switch connected to one of the plurality of ports used to receive microwaves from the resonance chamber, a phase shifter connected to the fast microwave switch, a tunable band pass filter connected to the phase shifter, and a microwave amplifier connected to the band pass filter and to the first one of the plurality of ports used to inject microwaves into the resonance chamber. This allows either the conductivity or sheet resistance or the carrier mobility of a thin film sample to be derived in the time domain.

BRIEF DESCRIPTION OF THE DRAWINGS

Embodiments of the present invention are described below, by way of only, with reference to the accompanying drawings, in which:

FIG. 9 is a cross-sectional view of the dielectric resonator of FIG. 1 in the x-z plane with tuning screws introduced into peripheral field regions of an electric field excited in the resonator;

DESCRIPTION OF THE PREFERRED EMBODIMENTS

Figure 1:
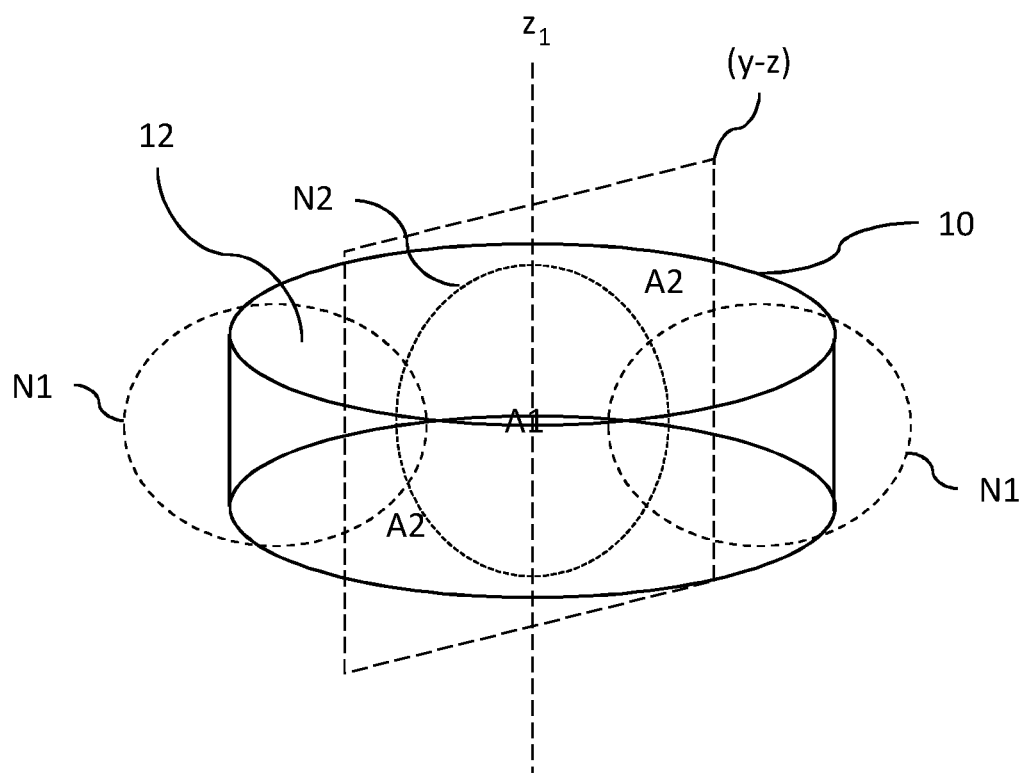
FIG. 1 is a perspective view of a dielectric resonator in the shape of a right circular cylinder of rotation about a symmetry axis, $z_1$.

Referring firstly to FIG. 1, there is shown a dielectric resonator 10 having a top surface 12. In this embodiment, the dielectric resonator 10 is in the shape of a right circular cylinder of rotation about a first symmetry axis, $z_1$, although in alternative embodiments, it could be other shapes, such as a right prism having a square or rectangular top surface, provided that the resonator always has at least a first symmetry axis, $z_1$. The resonator 10 is made of a single crystal of a high permittivity material with a low microwave loss tangent, such as sapphire, which has a relative permittivity of 11.6 on its c crystallographic axis and of 9.4 in its b-c crystallographic plane, and a microwave loss tangent of less than $10^{-5}$. The dielectric resonator 10 is grown so that the a crystallographic axis is aligned with the first symmetry axis, $z_1$, of the resonator.

The dielectric resonator 10 is made with a width (or in this embodiment, a diameter) convenient to measure the carrier mobility, as well as the conductivity or equivalently, the sheet resistance of a thin film sample brought into proximity with the top surface 12 of the resonator, as described further below. In other words, the width of the resonator 10 should be sufficient to characterise the properties of the sample over a desired region of the sample. The height (or equivalently, the depth) of the resonator 10 in the direction of the first symmetry axis, $z_1$, is determined from the chosen width of the resonator via its permittivity. If the height of the resonator is too small relative to its width—in other words, if the resonator is too thin—the resonant frequency of the resonator increases, making it impractical to measure. The aspect ratio (i.e. the ratio of the width to the height) of the resonator is therefore chosen to be at most about 10:1, and preferably about 3:1, as shown in FIG. 1. On the other hand, giving the resonator an aspect ratio less than about 3:1 has the disadvantage that it takes longer to grow as a single crystal.

Figure 2:
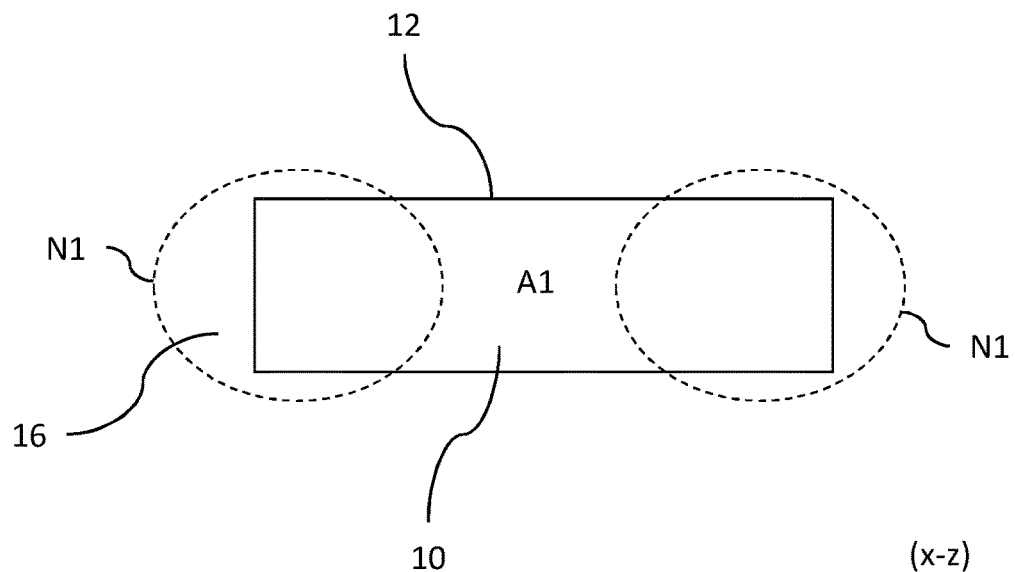
FIG. 2 is a cross-sectional view of the dielectric resonator of FIG. 1 in the x-z plane.
Figure 3:
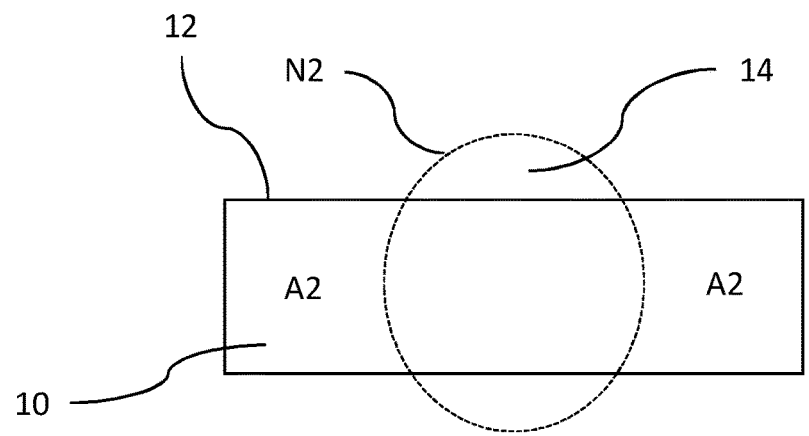
FIG. 3 is a cross-sectional view of the dielectric resonator of FIG. 1 in the y-z plane.
Figure 4:
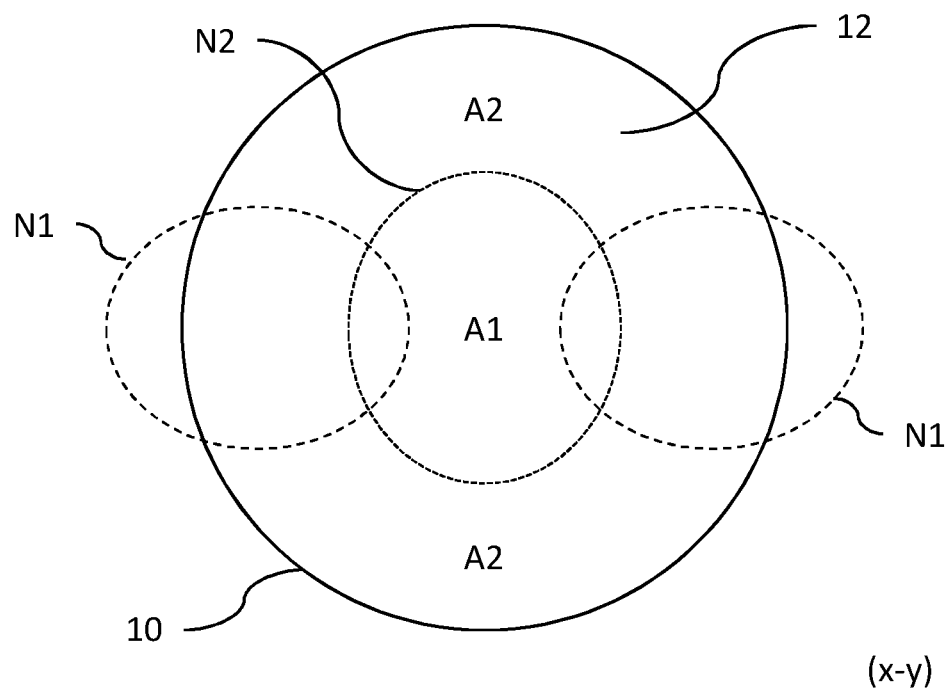
FIG. 4 is a top plan view of the dielectric resonator of FIG. 1 in the x-y plane.

When excited to resonate by the application of microwaves, the resonator 10 develops a $TE_{110}$ mode electric field, represented in FIG. 1 as follows. A first mode with two nodes respectively contained at the centre of each of two regions labelled N1 in FIG. 1 and an anti-node A1 located therebetween is excited in the x-z plane, and a second, orthogonal mode with two anti-nodes labelled A2 and a node located therebetween at the centre of a region labelled N2 is excited in the y-z plane. This $TE_{110}$ mode electric field may be more clearly seen in FIGS. 2 to 4, which respectively represent cross-sectional slices through the resonator of FIG. 1 in the x-z plane, the y-z plane and the x-y plane. FIG. 2 shows the first mode with two nodes in regions N1 and an anti-node A1 therebetween in the x-z plane, FIG. 3 shows the second, orthogonal mode with two anti-nodes A2 and a node in region N2 therebetween in the y-z plane, and FIG. 4 shows the orthogonality of both of these modes more clearly. As may be seen in all of FIGS. 1, 2 and 4, the regions labelled N1 respectively containing the nodes of the first mode extend beyond the circumference of resonator 10 into respective peripheral field regions 16, and as may be seen from both FIGS. 1 and 3, the region labelled N2 containing the node of the second mode extends above top surface 12 of resonator 10 into a near-field region 14, and equivalently below a bottom surface of resonator 10.

Figure 5:
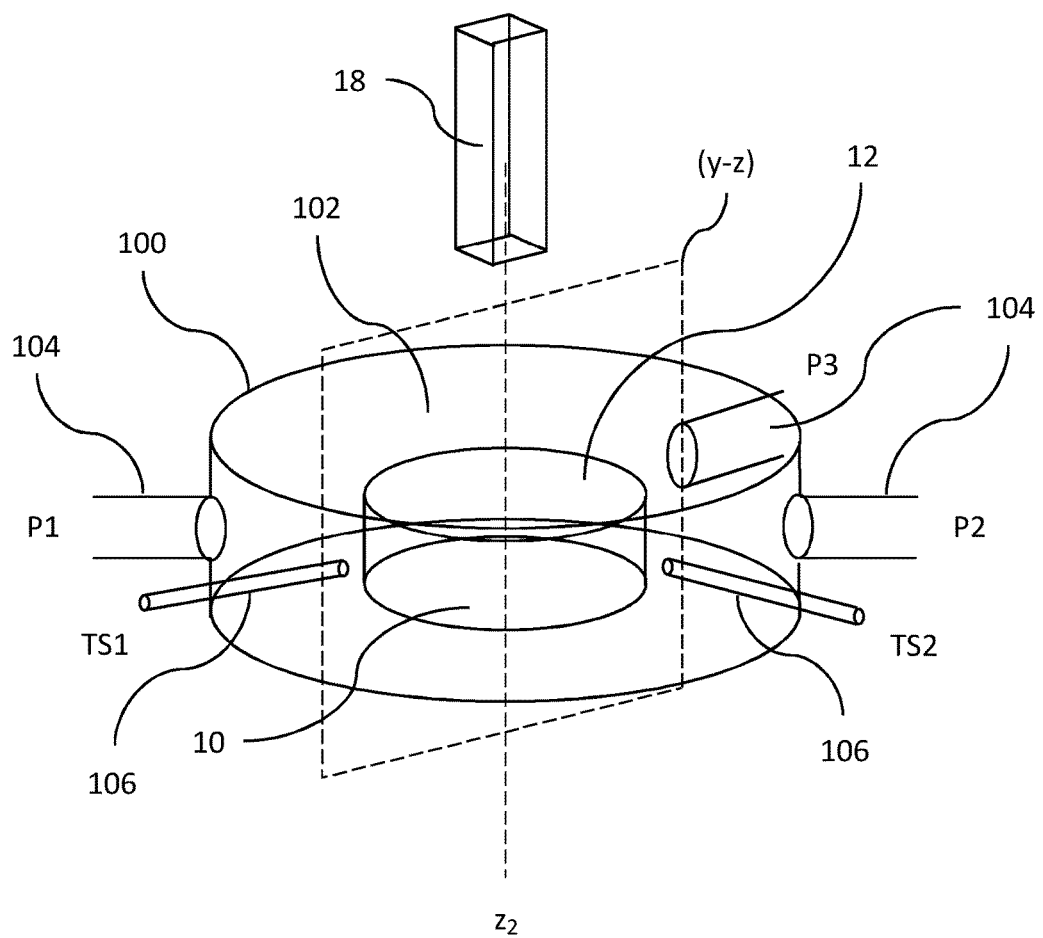
FIG. 5 is a perspective view of a resonance chamber containing and geometrically similar to the dielectric resonator of FIG. 1.

FIG. 5 shows the dielectric resonator 10 of FIGS. 1 to 4 located in an electrically conductive resonance chamber 100. The walls of the resonance chamber 100 are made of a high conductivity material, such as copper or aluminium, although it could, in principle, instead be made of another high conductivity material, such as gold, if this were not excluded on cost grounds. In this embodiment, the resonance chamber 100 is also a right circular cylinder of rotation about a second symmetry axis, $z_2$, and is therefore geometrically similar to the resonator 10. The resonator 10 is positioned in the resonance chamber 100 so that the first symmetry axis, $z_1$, of the resonator 10 is coincident with the second symmetry axis, $z_2$, of the resonance chamber 100. Apart from being geometrically similar to the resonator 10, the size of the resonance chamber 100 is chosen to be sufficiently greater than the size of the dielectric resonator 10 so as not to compromise the Q-factor of the resonator. In other words, if the resonance chamber 100 were to be made too small, it would start to impinge on one or both of the near-field region 14 and the peripheral field regions 16 of the resonator 10 shown in FIGS. 2 and 3. On the other hand, making the resonance chamber 100 any larger than about twice the size of the resonator 10 in any linear dimension, as shown in FIG. 5, is unnecessary.

Figure 6:
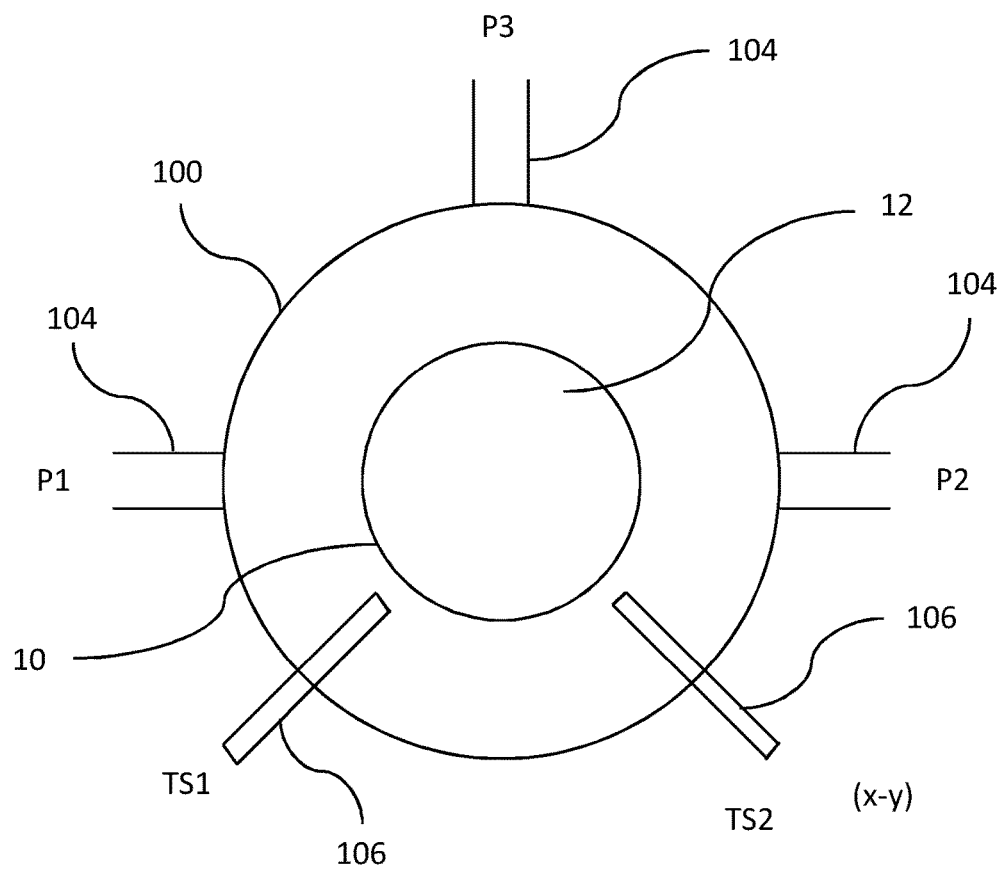
FIG. 6 is a top plan view in the x-y plane of the resonance chamber of FIG. 5 containing the dielectric resonator of FIG. 1.

As may be seen from FIG. 5, the resonance chamber 100 has a plurality of ports 104, which are similar to each other and are located orthogonal to the second symmetry axis, $z_2$, of the resonance chamber 100, and are therefore also orthogonal to the first symmetry axis, $z_1$, of the resonator 10. This may be seen more clearly in the top plan view of FIG. 6, which is a view of the resonance chamber 100 in the x-y plane. Each such port 104 has a microwave antenna (which, for improved clarity, are not shown in FIG. 5), either to inject microwaves into the resonance chamber 100, and thereby to excite an electric field in the resonator 10, or to receive microwaves from the resonance chamber 100. In this embodiment, the port labelled P1 in FIGS. 5 and 6 is to inject microwaves into the resonance chamber 100 and the two other ports labelled P2 and P3 in FIGS. 5 and 6 are to receive microwaves from the resonance chamber 100. As may be seen in the top plan view of FIG. 6, one (P2) of the ports 104 to receive microwaves from the resonance chamber 100 is located opposite the one (P1) of the ports 104 used to inject microwaves into the resonance chamber, with the resonator 10 located therebetween, whilst another one (P3) of the ports 104 to receive microwaves from the resonance chamber 100 is located orthogonal to the port P1 used to inject microwaves into the resonance chamber. The receiving port P2 opposite the port P1 used to inject microwaves into the resonance chamber is useful to measure the conductivity or equivalently, the sheet resistance of a thin film sample brought into proximity with the top surface 12 of the resonator and the receiving port P3 orthogonal to the port P1 used to inject microwaves into the resonance chamber is useful to measure the carrier mobility of such a sample, both in a manner as described further below.

Figure 7:
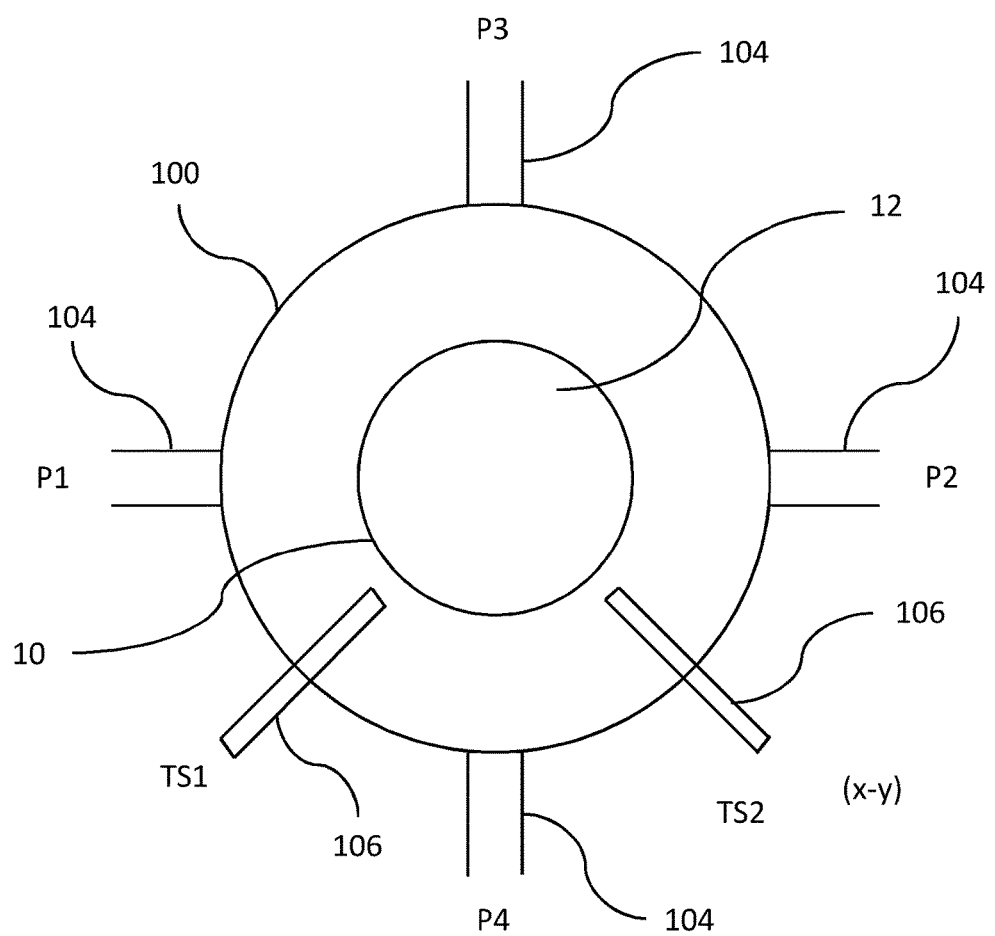
FIG. 7 is a top plan view in the x-y plane of an alternative embodiment of a resonance chamber containing the dielectric resonator of FIG. 1.

In another embodiment shown in FIG. 7, the resonance chamber 100 may comprise an additional receiving port, labelled P4 in FIG. 7, located opposite the receiving port P3, with the resonator 10 located therebetween. The additional receiving port P4 in such a location is also useful to measure the carrier mobility of a thin film sample brought into proximity with the top surface 12 of the resonator in a different direction from P3, but without the need to reverse the sample.

Figure 8A:
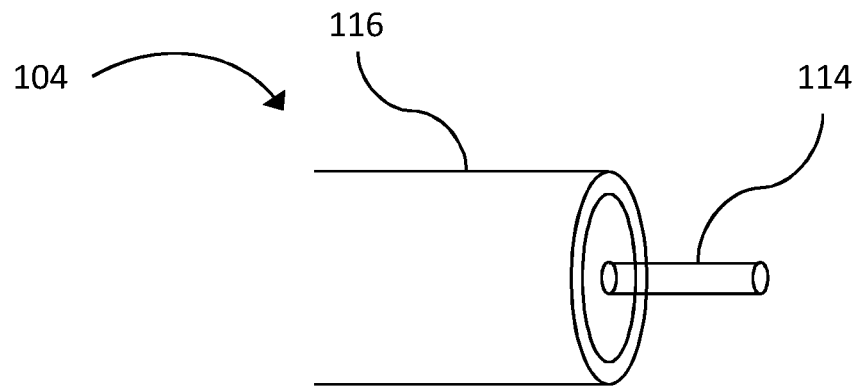
FIG. 8A shows a straight mode microwave antenna.
Figure 8B:
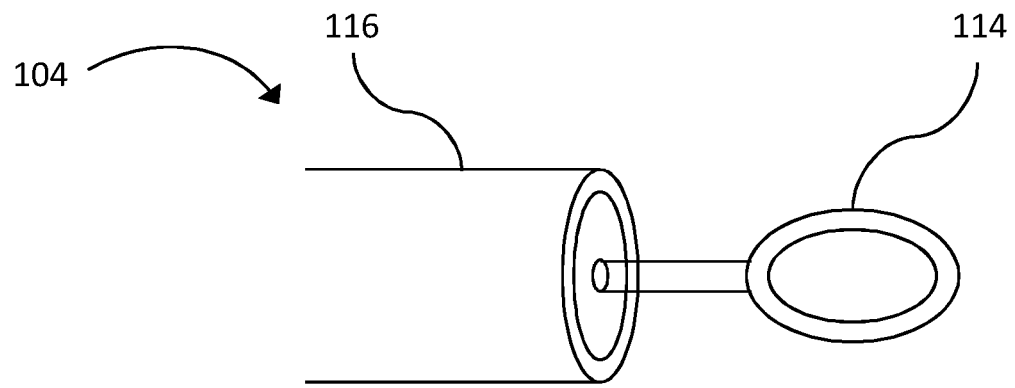
FIG. 8B shows a wire loop microwave antenna.

Examples of the microwave antennae 114 of ports 104 are respectively shown in FIGS. 8A and 8B. FIG. 8A shows a straight mode microwave antenna and FIG. 8B shows a wire loop microwave antenna. In both cases, the antenna 114 is formed from the conductive core of a coaxial cable and the conductive shielding 116 of the cable is brought into electrical contact with the resonance chamber 100.

Returning to FIG. 5, it may be seen that two electrically conductive tuning screws 106 are in electrical contact with the resonance chamber 100. Each tuning screw is at least partially positionable in the electric field excited in the resonator 10. As may be seen in both FIGS. 6 and 7, the tuning screws 106 are mounted to the resonance chamber 100 coplanar with the plurality of ports 104, each tuning screw 106 being mounted about the first symmetry axis, $z_1$, at an angle of 45 degrees to a respective one of the plurality of ports 104. Thus, the tuning screw labelled TS1 in FIGS. 5 to 7 is mounted at an angle of 45 degrees about the first symmetry axis, $z_1$, to the port P1 used to inject microwaves into the resonance chamber 100, and the tuning screw labelled TS2 in FIGS. 5 to 7 is mounted at an angle of 45 degrees about the first symmetry axis, $z_1$, to the port P2 used to receive microwaves from the resonance chamber. The tuning screws 106 are each at least partially positionable in the electric field of the resonator 10 by being turned on a respective screw thread. Turning one of the tuning screws 106 clockwise or anticlockwise on its respective screw thread in this manner advances the tuning screw into or retracts the tuning screw from one of the peripheral field regions 16 of the resonator 10, as shown in FIG. 9. Since the tuning screws 106 are in electrical contact with the resonance chamber 100, the electric field excited in the resonator 10 is slightly altered or tweaked thereby, which may be used to ensure that the orthogonal first and second modes of the electric field displayed in FIGS. 1 to 4 are degenerate with each other. By "degenerate" is meant that the two orthogonal modes both fall within the line width of the resonant frequency of resonator 10. This degeneracy may be ensured by detecting a node at port P2 and an antinode at port P3 when microwaves are injected via port P1 into the resonance chamber 100 at the resonant frequency of the resonator 10. In this way, any slight and inevitable asymmetries in either the manufacture of the dielectric resonator 10 or in the set-up of the resonator within the resonance chamber 100, or both, may be compensated for and eliminated by adjusting the positions of the tuning screws.

Another embodiment, providing simpler but less accurate measurement, uses only a single mode. In this embodiment the transmitted microwave power from one port to a parallel port is measured under two conditions: 1) with no applied magnetic field and 2) with a magnetic field applied along the dielectric resonator symmetry axis. The fractional difference in transmitted power is proportional to the mobility of the thin film and to the square of the magnetic field so this measurement may also be used to estimate the thin film mobility. The square law dependence on magnetic field makes this a less sensitive method than the one outlined above but it is simpler since no careful adjustment of tuning screws is required to ensure the orthogonality of two degenerate modes.

Finally, it may also be seen from FIG. 5 that associated with the resonance chamber 100, is a source of magnetism 18 for applying a magnetic field to a thin film sample brought into proximity with the top surface 12 of the resonator 10 substantially parallel or anti-parallel to the first symmetry axis, $z_1$, in order to measure the carrier mobility of the sample, as described further below. The source 18 may be a permanent magnet or an electromagnet. If it is an electromagnet, this allows the carrier mobility of the sample to be determined under the conditions of a time varying, magnitude varying, or possibly even reversing magnetic field.

Resonance chamber 100 may completely enclose dielectric resonator 10, in which case, since resonance chamber 100 is electrically conductive, it will act as a Faraday cage. If the source of magnetism 18 is intended to apply a static or slowly varying magnetic field of up to about 100 kHz to a thin film sample brought into proximity with the top surface 12 of the resonator 10 (for example, if the source of magnetism 18 is a permanent magnet), then this is unproblematic and the magnetic field can penetrate the Faraday cage of resonance chamber 100 and reach the sample. However, if the source of magnetism 18 is instead intended to apply a more rapidly varying magnetic field to a thin film sample brought into proximity with the top surface 12 of the resonator 10, then such a magnetic field would otherwise be blocked by the Faraday cage from reaching the sample, and must therefore be allowed to gain access to the sample. In such a case, the resonance chamber 100 need not completely enclose dielectric resonator 10 and may instead be provided with a point of entry or window for the magnetic field to the resonance chamber 100.

Furthermore, resonance chamber 100 may alternatively or additionally comprise an opening 102 allowing a sample to be introduced to the near-field region 14 of the electric field excited in the resonator 10 within resonance chamber 100. If so, a variety of samples may be brought into proximity with the top surface 12 of the resonator 10 in quick succession or even a continuous web of sample material may be passed through proximity with the top surface 12 of the resonator 10. For example, if a thin film of a material such as graphene is grown or transferred onto a continuous web of a flexible substrate, such as a polymer like polyethylene terephthalate (PET), the web may be passed through proximity with the top surface 12 of the resonator 10 (say, within 20 mm thereof) after the flexible substrate with the thin film thereon emerges from a growth or transfer chamber. Such a procedure could be used for manufacturing quality control, by performing measurements of the carrier mobility or of the conductivity or sheet resistance of the thin film at intervals of as little as 1 millisecond. Moreover, the resonator 10 may be positioned within the resonance chamber 100 in such a way that the near-field region 14 of the electric field excited in the resonator 10 extends beyond the opening 102 of the resonance chamber 100. In such a case, a variety of samples or a continuous web of sample material may be introduced to the near-field region 14 of the electric field excited in the resonator 10 without even having to enter the resonance chamber 100.

As shown, opening 102 replaces the entire top surface of the resonator housing. However, the opening may be smaller than this, depending upon the application, and may be of any desired shape.

If the web of material is wider than a single dielectric resonator, an array of similar resonators may be deployed at right angles to the movement of the web from the production line, so that the entire width of the material may be measured simultaneously. The inevitable small gaps between adjacent resonators may be covered by providing a second array of dielectric resonators, parallel to the first and offset slightly in the direction of movement of the web but also offset slightly in the direction parallel to the array, so that there are not parts of the web which do not pass over a dielectric resonator.

In the event that the web movement is too fast to allow the magnetic field (required to measure the mobility) to be turned on and off rapidly enough to provide accurate measurements, two dielectric resonators or two parallel arrays of dielectric resonators are employed. A constant magnetic field is applied to one array, whereas no magnetic field is applied to the other. Then movement of the web from one array to the other causes each part of the web to be moved from finite applied magnetic field to zero applied magnetic field, without the need to switch one and off the magnetic field.

In-line or roll-to-roll application of the method used in connection with a web allows very rapid real-time measurement of the graphene film being grown/transferred on a high speed production line while being monitored with the microwave system. This provides a fast means to detect (and possibly rectify) any problems occurring in the graphene production line.

Figure 10A:
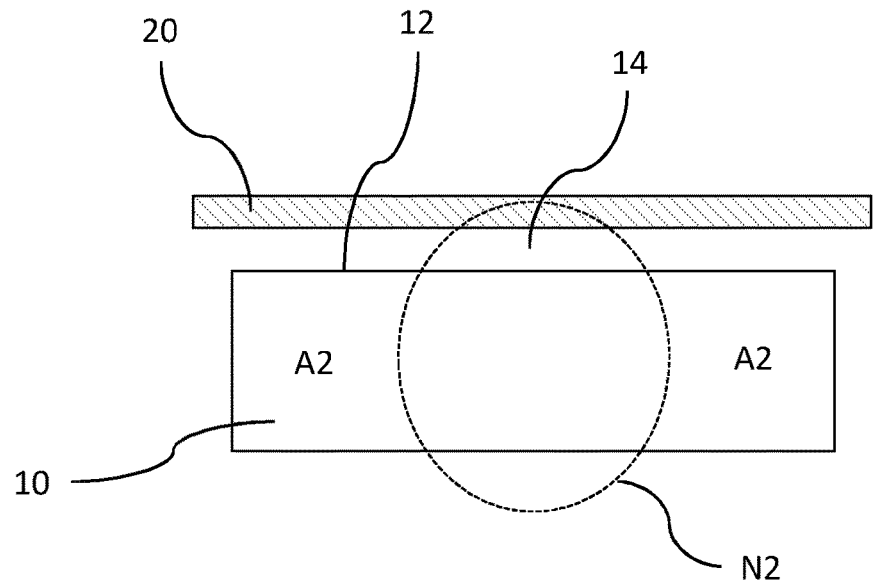
FIG. 10A is a cross-sectional view of the dielectric resonator of FIG. 1 in the y-z plane with a bare substrate introduced into a near-field region of an electric field excited in the resonator.
Figure 10B:
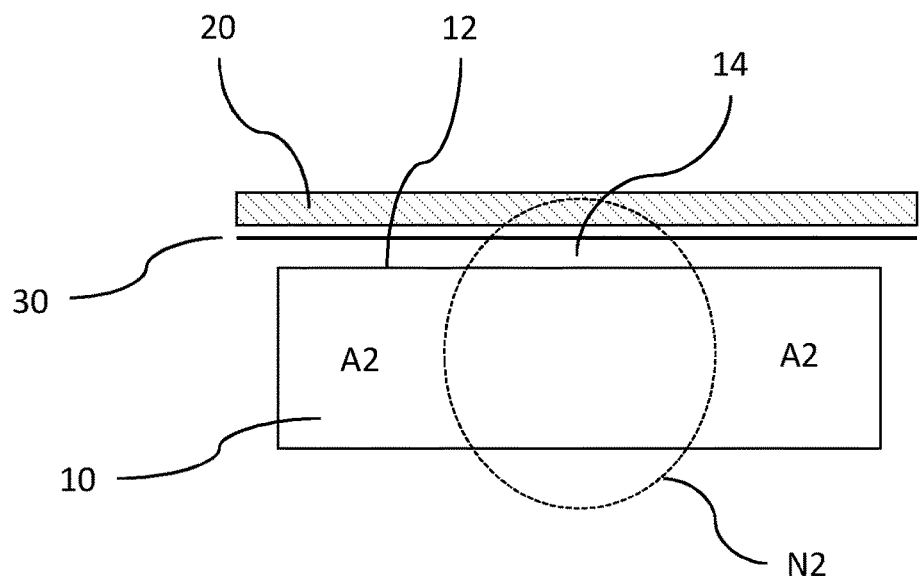
FIG. 10B is a cross-sectional view of the dielectric resonator of FIG. 1 in the y-z plane with a substrate having a thin film formed on one side thereof introduced into a near-field region of an electric field excited in the resonator.

Turning next to FIGS. 10A and 10B, there is shown how to measure the conductivity or sheet resistance of a thin film sample using a measuring device comprising a resonator of the type shown in FIG. 1 contained within a resonance chamber of the type shown in either of FIGS. 5 and 7. Firstly, microwaves are injected into the resonance chamber 100 via the first one P1 of the plurality of ports 104, in order to excite an electric field in the resonator 10. A bare substrate 20 is then introduced into the near-field region 14 of the electric field thereby excited in the resonator, in the manner shown in FIG. 10A. In this condition, microwaves are received from the resonance chamber 100 via the port P2 of the plurality of ports 104 opposite to port P1, and a first resonant frequency and a first line width of the peak output power of the microwaves received via the port P2 are measured. The bare substrate 20 is then removed from the near-field region 14 of the electric field excited in the resonator and replaced with a like substrate 20 having the thin film sample 30 formed thereon in the same location in the near-field region 14 of the electric field excited in the resonator as was previously occupied by the bare substrate 20, as is shown in FIG. 10B. Once again, microwaves are received from the resonance chamber 100 via the port P2 and a second resonant frequency and a second line width of the peak output power of the microwaves received via port P2 are measured. The first and second resonant frequencies and the first and second line widths are then compared with each other, in a manner to be described further below, in order to derive the conductivity or sheet resistance of the thin film sample.

Figure 10C:
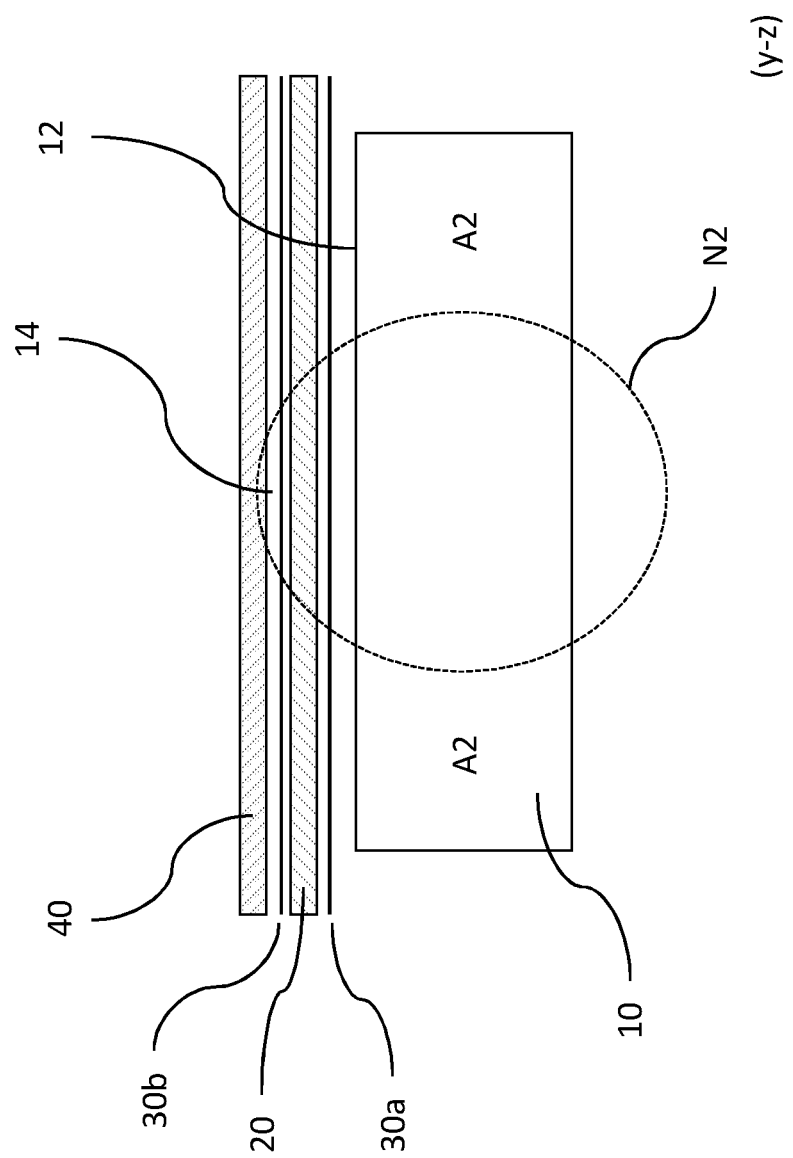
FIG. 10C is a cross-sectional view of the dielectric resonator of FIG. 1 in the y-z plane with a substrate having a thin film formed on both sides thereof introduced into a near-field region of an electric field excited in the resonator.

In another embodiment, as shown in FIG. 10C, when the bare substrate 20 is removed from the near-field region 14 of the electric field excited in the resonator 10, it may instead be replaced with a like substrate 20 having a first thin film 30a formed on a first side thereof and a second thin film 30b formed on a second side thereof in the same location in the near-field region 14 of the electric field excited in the resonator as was previously occupied by the bare substrate 20. This may be the case, for example, when thin-film samples of graphite comprising monolayers and very few layers of graphene are grown on a substrate of silicon carbide (SiC), which results in graphene layers on both opposing sides of the substrate. However, if the second thin film 30b is brought into contact with an electrical conductor 40, as is also shown in FIG. 10C, then when microwaves are received from the resonance chamber 100 via the port P2, and the second resonant frequency and the second line width of the peak output power of the microwaves received via port P2 are measured, these will only represent a contribution of the first thin film 30a formed on the first side of the like substrate 20, since any contribution from the second thin film 30b is shorted out by being in contact with the electrical conductor 40. This has the advantage that the conductivity or sheet resistance of the first thin film 30a may therefore be derived, even in the presence of the second thin film 30b but without interference from the latter.

Since the near-field region 14 of the electric field excited in the resonator 10 extends beyond the top surface 12 of the resonator 10, it is not actually necessary to bring either the bare substrate 20 or the like substrate 20 with either a thin film sample 30 formed thereon or having a first thin film 30a formed on a first side thereof and a second thin film 30b formed on a second side thereof into contact with the top surface 12 of the resonator 10, in order to create a difference between the first and second resonant frequencies and the first and second line widths of the peak output power of the microwaves received via port P2, from which the conductivity or sheet resistance of the thin film can be derived. Instead, the steps of introducing the bare substrate 20 into the near-field region 14 of the electric field excited in the resonator 10 and introducing the like substrate 20 having a thin film 30, 30a, 30b formed thereon into the same location may both be conducted without contacting the resonator 10 with either the substrate 20 or the thin film 30, 30a, 30b. This has the advantage that the measurement of the conductivity or sheet resistance of the thin film may be carried out in a non-invasive and non-destructive manner, which preserves the thin film sample unchanged by the measurement process.

On the other hand, it is now also possible to measure the carrier mobility of a thin film sample using a measuring device comprising a resonator of the type shown in FIG. 1 contained within a resonance chamber of the type shown in either of FIGS. 5 and 7. If so, microwaves are firstly injected into the resonance chamber 100 via the first one P1 of the plurality of ports 104, as before, in order to excite an electric field in the resonator 10. However, in this case, instead of being received from the resonance chamber 100 via the port P2 which is opposite to port P1, the microwaves are received from the resonance chamber 100 via one of the ports P3, P4 of the plurality of ports 104 which is orthogonal to port P1, and a position of one or more of the tuning screws 106 in the electric field excited in the resonator 10 is adjusted until the microwaves received from the resonance chamber 100 via the orthogonal port P3, P4 is found to be at a minimum at the resonant frequency of the resonator 10. This shows that a first mode (N1, A1, N1) of the electric field is degenerate with a second mode (A2, N2, A2) thereof orthogonal to the first mode, as described above in relation to FIG. 9.

Once this orthogonality condition has been met, a substrate 20 having a thin film sample 30 formed thereon is introduced into the near-field region 14 of the electric field, as is shown in FIG. 10B. With the substrate and the sample now in place, microwaves are again received from the resonance chamber 100 via one of the ports P3, P4 of the plurality of ports 104 which is orthogonal to port P1, and a first peak output power of the microwaves received via the orthogonal port P3, P4 is measured. Then, whilst the source of magnetism 18 is used to apply a magnetic field to the substrate 20 having the thin film 30 formed thereon which is substantially parallel or anti-parallel to the first symmetry axis, $z_1$, of the resonator 10, microwaves are again received from the resonance chamber 100 via the orthogonal port P3, P4, and a second peak output power of the microwaves received via that orthogonal port is measured. The first and second peak output powers are then compared with each other, in a manner to be described further below, in order to derive the carrier mobility of the thin film.

As before, a measuring device comprising a resonator of the type shown in FIG. 1 contained within a resonance chamber of the type shown in either of FIGS. 5 and 7 may also be used to measure the carrier mobility of a first thin film 30a formed on a first side of a substrate 20 having a second thin film 30b formed on a second side thereof, as is shown in FIG. 10C, without any contribution from the second thin film 30b, if the second thin film 30b is brought into contact with an electrical conductor 40, as is also shown in FIG. 10C. Then, when microwaves are received from the resonance chamber 100 via the orthogonal port P3, P4, and the first and second peak output powers of the microwaves received via the orthogonal port P3, P4 are measured, these will only represent a contribution of the first thin film 30a formed on the first side of substrate 20, since any contribution from the second thin film 30b is shorted out by being in contact with the electrical conductor 40. Thus the carrier mobility of the first thin film 30a may also be derived, even in the presence of the second thin film 30b, but without interference from the latter.

Once again, since the near-field region 14 of the electric field excited in the resonator 10 extends beyond the top surface 12 of the resonator 10, it is not actually necessary to bring the substrate 20 with either a thin film sample 30 formed thereon or having a first thin film 30a formed on a first side thereof and a second thin film 30b formed on a second side thereof into contact with the top surface 12 of the resonator 10, in order to create a difference between the first and second peak output powers of the microwaves received via the orthogonal port P3, P4, from which the carrier mobility of the thin film can be derived. Instead, the step of introducing the substrate 20 having a thin film 30, 30a, 30b formed thereon into the near-field region 14 of the electric field excited in the resonator 10 may be conducted without contacting the resonator 10 with either the substrate 20 or the thin film 30, 30a, 30b. This has the advantage that the measurement of the carrier mobility of the thin film may be carried out in a non-invasive and non-destructive manner, which preserves the thin film sample unchanged by the measurement process.

It will now be described, in relation to FIGS. 11 to 13, how the conductivity or sheet resistance of a thin film sample may be derived from the first and second resonant frequencies and the first and second line widths of the microwaves received from the resonance chamber 100 via the port P2 opposite to port P1, and how the carrier mobility of a thin film sample may be derived from the first and second peak output powers of the microwaves received from the resonance chamber 100 via one of the orthogonal ports P3, P4, using a comparator circuit as shown in either FIG. 11 or FIG. 12.

Figure 11:
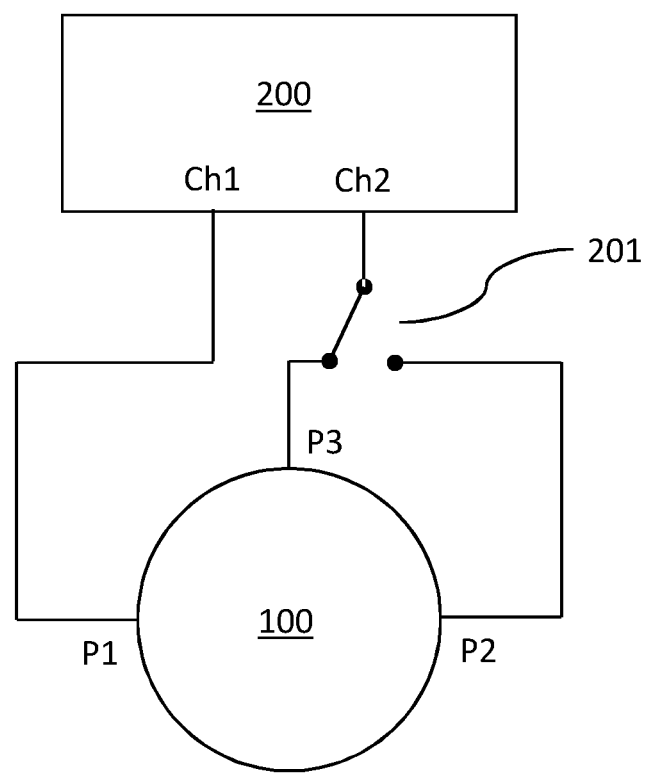
FIG. 11 is a schematic diagram of a measuring device according to a first embodiment of the invention, comprising the resonance chamber of FIG. 5 containing the dielectric resonator of FIG. 1 and connected to a comparator circuit comprising a vector network analyser.

FIG. 11 shows a comparator circuit for deriving either the conductivity or sheet resistance or the carrier mobility of a thin film sample in the frequency domain. Thus the comparator circuit of FIG. 11 comprises a vector network analyser (VNA) 200 with channels Ch1, Ch2 respectively connected to the first one P1 of the plurality of ports 104 used to inject microwaves into the resonance chamber 100 and another P2, P3, P4 of the plurality of ports 104 used to receive microwaves from the resonance chamber. Channel Ch2 may be connected either to the port P2 opposite to port P1 or to one of the orthogonal ports P3, P4 via a two-way switch 201. The vector network analyser 200 may therefore be used as desired either to measure, record and/or display the first and second resonant frequencies and the first and second line widths of the microwaves received from the resonance chamber 100 via the port P2 opposite to port P1, in order to derive the conductivity or sheet resistance of the thin film sample in a manner to be described below in relation to FIG. 13, or to measure, record and/or display the first and second peak output powers of the microwaves received from the resonance chamber 100 via one of the orthogonal ports P3, P4, in order to derive the carrier mobility of the thin film sample in a manner as will also be described below in relation to FIG. 13.

Figure 12:
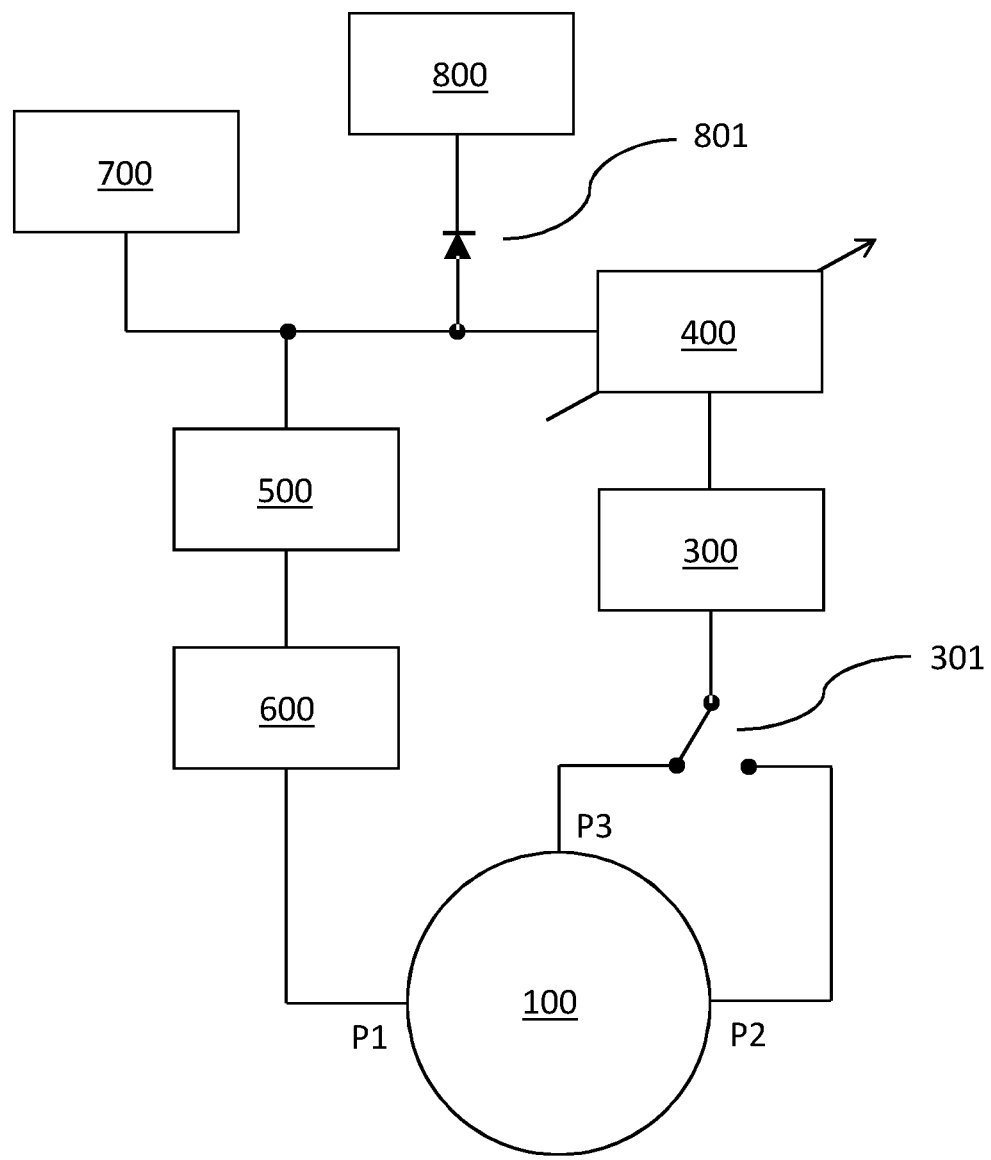
FIG. 12 is a schematic diagram of a measuring device according to a second embodiment of the invention, comprising the resonance chamber of FIG. 5 containing the dielectric resonator of FIG. 1 and connected to a comparator circuit comprising a loop oscillator.

On the other hand, FIG. 12 shows a comparator circuit for deriving either the conductivity or sheet resistance or the carrier mobility of a thin film sample in the time domain. The comparator circuit of FIG. 12 includes a loop oscillator comprising a fast microwave switch 300 connected to one P2, P3, or P4 of the plurality of ports 104 used to receive microwaves from the resonance chamber 100, a phase shifter 400 connected to the fast microwave switch 300, a tunable band pass filter 500 connected to the phase shifter 400, and a microwave amplifier 600 connected to the band pass filter 500 and to the first one P1 of the plurality of ports 104 used to inject microwaves into the resonance chamber 100. Thus, the loop oscillator is connected in a loop both to the first one P1 of the plurality of ports 104 used to inject microwaves into the resonance chamber 100 and to one P2, P3, or P4 of the plurality of ports 104 used to receive microwaves from the resonance chamber, but the latter connection may be rapidly broken or restored by placing the fast microwave switch 300 respectively into an open or "off", or a closed or "on" position.

The loop oscillator works by amplifying thermal noise in the resonance chamber 100, the output from the amplifier 600 being fed back into the input port P1, so that the loop oscillator resonates on one of the resonant modes of the dielectric resonator 10. The fast microwave switch 300 comprises a plurality of p-i-n diodes, which give about 90 dB of isolation when fast switch 300 is placed into the open or "off" position. This stops the resonance in the loop oscillator virtually instantaneously (with a decay time of about 1 to 5 microseconds), which allows the fast switch 300 to be placed back into the closed or "on" position after a period of less than about 10 microseconds. The resonance in the loop oscillator then rapidly builds up again, allowing the process to be repeated at intervals of as little as about 1 millisecond. This allows the conductivity or sheet resistance or the carrier mobility of one or more thin film samples to be measured repeatedly and in rapid succession one or more times in each cycle of resonance.

Like the VNA 200 of FIG. 11, the loop oscillator of FIG. 12 may be connected either to the port P2 opposite to port P1 or to one of the orthogonal ports P3, P4 via a two-way switch 301. This allows the loop oscillator to be used as desired either to measure the first and second resonant frequencies and the first and second line widths of the microwaves received from the resonance chamber 100 via the port P2 opposite to port P1, in order to derive the conductivity or sheet resistance of the thin film sample in a manner to be described below in relation to FIG. 13, or to measure the first and second peak output powers of the microwaves received from the resonance chamber 100 via one of the orthogonal ports P3, P4, in order to derive the carrier mobility of the thin film sample in a manner as will also be described below in relation to FIG. 13.

In order to allow these measurements to be carried out, the loop oscillator is itself in turn connected to at least one of a counter 700 and an oscilloscope 800, the latter of which is preferably isolated from the loop oscillator by means of a diode 801, to prevent feedback from the oscilloscope 800 to the loop oscillator. The first and second resonant frequencies of the microwaves received from the resonance chamber 100 may then be measured in a straightforward fashion by means of the counter 700. On the other hand, the first and second line widths of the microwaves are measured by means of the fast microwave switch 300, since when fast switch 300 is placed in the open or "off" position, the time constant for exponential decay of the resonance which has built up in the loop oscillator is inversely proportional to the bandwidth of the resonance, and the resonance may be displayed on the oscilloscope 800 to measure this line width. The first and second peak output powers may also be displayed and measured on the oscilloscope 800.

The comparison of the first and second resonant frequencies and the first and second line widths, as well as of the first and second peak output powers, may be carried out from the measurements made with the comparator circuit of either FIG. 11 or FIG. 12, in order to derive the conductivity or sheet resistance of the thin film sample on the one hand or the carrier mobility of the thin film sample on the other, in the following manner.

Figure 13:
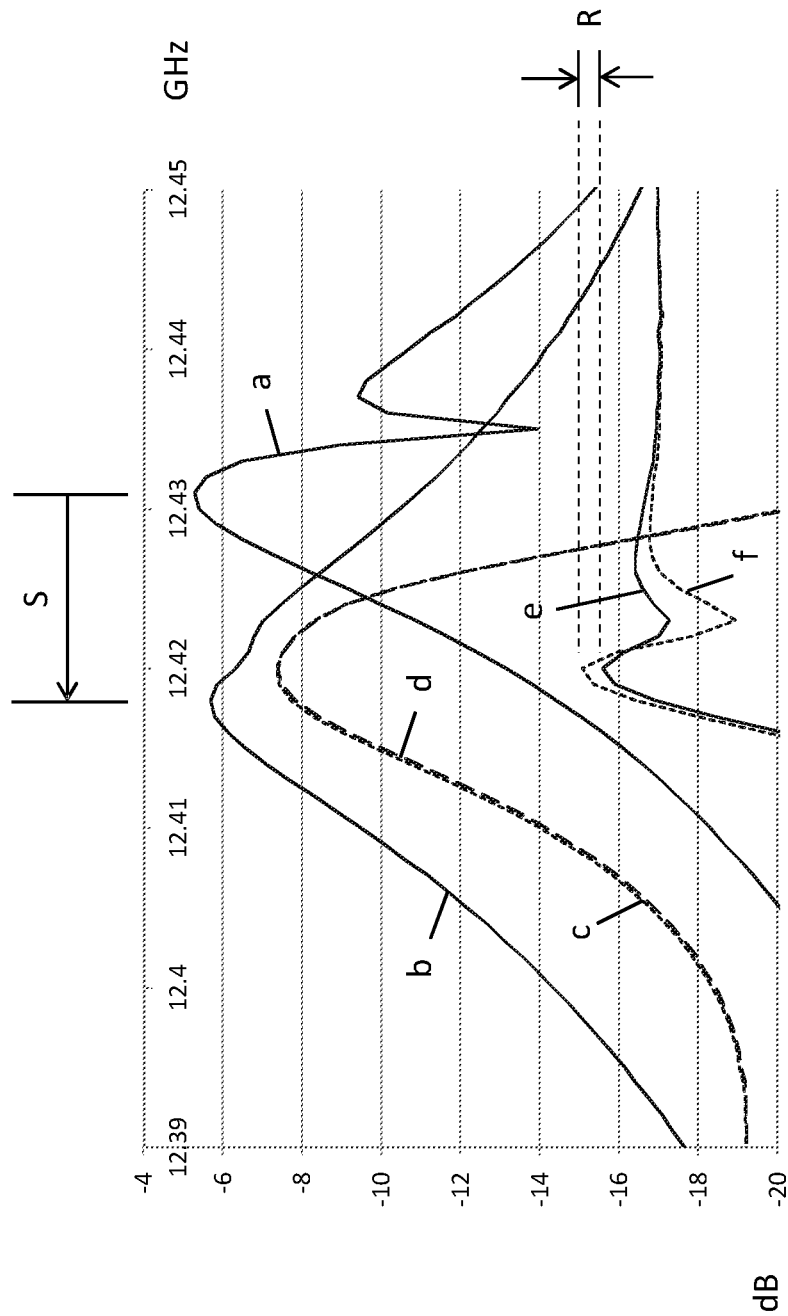
FIG. 13 is a graph showing an example of experimental results obtained with a measuring device according to an embodiment of the invention.

Referring now to the graph of FIG. 13, six different curves on this graph show the microwave power output at one of the plurality of ports 104 used to receive microwaves from the resonance chamber 100 when microwaves are introduced into the chamber 100 via port P1. These six curves may best be understood as three pairs of curves, respectively labelled a and b, c and d, and e and f in FIG. 13, wherein the two members of each pair of curves may be compared with each other. The first pair of curves a and b shows how to measure the conductivity (or equivalently, sheet resistance) of a thin-film sample 30 from the microwave power received at port P2 opposite P1. The second pair of curves c and d shows the null effect on the microwave power received at port P3, P4 orthogonal to P1 when a magnetic field is applied to the resonator 10 in the absence of such a thin-film sample. The third pair of curves e and f shows how to measure the carrier mobility of the thin-film sample 30 from the microwave power received at port P3, P4 orthogonal to P1.

Thus, curve a firstly shows the microwave power received at port P2 opposite P1 when the chamber is empty. In contrast, curve b shows the equivalent microwave power received at port P2 when a thin-film sample 30 is introduced into the near-field region 14 of the electric field excited in the resonator 10. Comparison of curves a and b shows a shift in frequency, labelled S in FIG. 13, in the peak output power between curves a and b, as well as a broadening of the peak of curve b relative to curve a, which may then both be used to derive the conductivity (or equivalently, sheet resistance) of the sample. The mathematical technique for deriving the conductivity or sheet resistance of the sample from the shift in frequency S and the difference in the line widths of curves a and b is described in the inventors' paper "Non-contact method for measurement of the microwave conductivity of graphene" in Applied Physics Letters, Vol. 103, pp. 123103-1-123103-4 (2013), already referred to above.

Curve c, marked in dotted lines, shows the microwave power instead received at port P3, P4 orthogonal to P1 when a bare substrate 20 is introduced into the near-field region 14 of the electric field excited in the resonator 10, as shown in FIG. 10A, but when no magnetic field is applied to resonator 10. In contrast, curve d, marked in dashed lines in order to help distinguish it more clearly from curve c, shows what happens when a magnetic field is then applied to resonator 10. Comparison of curves c and d shows that when this magnetic field is applied, there is no change in either the frequency of the peak output power or the shape of the microwave power output received at port P3, P4, curves c and d being, to all intents and purposes, indistinguishable from each other. This confirms that in the absence of a thin-film sample 30 being introduced into the near-field region 14 of the electric field excited in the resonator 10, the application of a magnetic field has no effect on the response measured at P3, P4.

Finally, curve e shows the microwave power received at port P3, P4 when a substrate 20 having a thin film 30 formed on one side thereof is introduced into the near-field region 14 of the electric field excited in the resonator 10, as shown in FIG. 10B, and when no magnetic field is applied to resonator 10. In contrast, curve f, again marked in dashed lines in order to help distinguish it more clearly from curve e, shows what happens when a magnetic field is then applied to resonator 10. Comparison of curves e and f shows that when this magnetic field is applied, the peak output power of curve f increases by a small but measureable amount, labelled R in FIG. 13, relative to the peak output power of curve e. This increase in output power, which measures about 2.4% of the peak output power of curve b for an applied magnetic field of 20 mT, may then be used to derive the carrier mobility of the sample 30, since the ratio of the two peak output powers of curves e and f is proportional to the carrier mobility of the sample. The constant of proportionality may be determined by calibration against a measurement of the carrier mobility conducted on a similar sample using a conventional technique. For example, data measured using the present technique for a thin-film sample of graphene grown on copper by chemical vapour deposition (CVD) and then transferred to a quartz substrate is found to be in good agreement with data for similar films measured using a conventional technique involving patterning the film into a Hall bar device and applying electrical contacts to the device. In general, for a high quality graphene sample, such as those prepared on SiC, the carrier mobility at room temperature can be around $10^4$ cm$^2$V$^{-1}$ s$^{-1}$=1 m$^2$ Wb$^{-1}$. Thus, the application of a magnetic field of 0.1 T to the sample would result in a change of about 1% in the in-line conductivity of the sample, and a correspondingly measureable change in the peak output power received at port P3, P4, from which the carrier mobility can then be derived.

A measurement device as taught herein can allow all of the measurements described above to be carried out across a range of frequencies, according to the geometry which is chosen for resonator 10.

Moreover, with a measurement device as taught herein, all of the measurements described above may be carried out not only at room temperature, but also at elevated temperatures, as well as at reduced or even cryogenic temperatures. If they are carried out at elevated temperatures, they may be particularly suited to being used for quality control in manufacturing techniques for growing graphene and other two-dimensional materials. For example, by applying a time-varying, spatially uniform magnetic field to a thin film with a time resolution of as little as 1 millisecond, the carrier mobility of the film may be monitored on a similarly short timescale, allowing the growth or transfer parameters of the film to be controlled and varied in order to optimise the film quality and properties, and tailor the film to specific requirements and applications. On the other hand, if the measurements are carried out at low temperatures, they may be particularly suitable for characterizing the very high carrier mobility of graphene at such low temperatures and even for exploring the quantum Hall effects in graphene and other two-dimensional materials at cryogenic temperatures. Other applications of the measurement device are also likely, however, relating to the testing of two-dimensional materials in devices and systems dedicated to particular industrial applications.

Various modifications may be made to the described arrangements. For example, the tuning screws may be replaced by any other suitable tuning elements or tuning mechanism.

The term "comprising" as used herein is intended to be equivalent to "including".

The expression "bare substrate" means a substrate not having thereon any active film, such as a film of graphene.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The following technical information is also relevant to the present application.

In the Drude theory of the electrical conductivity of a metal, an electron is accelerated by the electric field for an average time τ, the relaxation time, before being scattered by impurities, lattice imperfections and phonons to a state which has average velocity zero.

The average drift velocity of the electron is $$v_d = \frac{-eE\tau}{m} \qquad (1)$$

where E is the electric field and m is the electron mass. The current density is thus $$j = -nev_d = \sigma_0 E$$

where $$\sigma_0 = \frac{ne^2\tau}{m}$$

and n is the electron carrier density.

In a metal or a semiconductor the electron mobility characterizes how quickly an electron can move when driven by an electric field. In semiconductors there is an analogous quantity for holes called hole mobility. The mobility μ is defined by the expression $$\mu = \frac{v_d}{E} = \frac{\sigma_0}{ne} \qquad (2)$$

In the presence of a steady magnetic field $B_z$, the conductivity and resistivity become tensors which are defined:—

$$\sigma = \begin{pmatrix} \sigma_{xx} & \sigma_{xy} \\ \sigma_{yx} & \sigma_{yy} \end{pmatrix}$$

$$\rho = \begin{pmatrix} \rho_{xx} & \rho_{xy} \\ \rho_{yx} & \rho_{yy} \end{pmatrix}$$

where the defining relationships are:

$$E = \rho \cdot j$$

$$j = \sigma \cdot E$$

In the presence of a magnetic field B the Lorentz force must be added to the force from the electric field in Eq. (1), $$v_d = -e(E + v_d \times B)\frac{\tau}{m}$$

In the steady state, $$j = -nev_d$$

Then in the xy plane $$\sigma_0 E_x = \omega_c \tau j_y + j_x$$

$$\sigma_0 E_y = -\omega_c \tau j_x + j_y$$

where $\sigma_0$ is defined above and $$\omega_c = \frac{eB}{m}$$

is the cyclotron frequency.

Substituting in the above we can get expressions for the resistivity and conductivity tensors:

$$\rho = \begin{pmatrix} \frac{1}{\sigma_0} & \frac{\omega_c \tau}{\sigma_0} \\ -\frac{\omega_c \tau}{\sigma_0} & \frac{1}{\sigma_0} \end{pmatrix}$$

$$\sigma = \begin{pmatrix} \frac{\sigma_0}{1+(\omega_c \tau)^2} & \frac{-\sigma_0 \omega_c \tau}{1+(\omega_c \tau)^2} \\ \frac{\sigma_0 \omega_c \tau}{1+(\omega_c \tau)^2} & \frac{\sigma_0}{1+(\omega_c \tau)^2} \end{pmatrix}$$

From these two expressions we can calculate how the presence of a d.c. magnetic field $B_z$ not only introduces an off-diagonal contribution to the (Hall) conductivity but it also reduces the diagonal conductivity by a small amount $$\rho_{xy} = \frac{\omega_c \tau}{\sigma_0} = \frac{B}{ne} = \frac{\mu B}{\sigma_0}$$

$$\sigma_{xy} \cong \sigma_0 \omega_c \tau = \sigma_0 \mu B$$

And the expression below estimates the fractional change in the diagonal conductivity $$\frac{\Delta \sigma_{xx}}{\sigma_0} = -\left(\frac{eB\tau}{m}\right)^2 = -(\mu B)^2$$

provided that the magnetic field $B \ll (m/e\tau) = 1/\mu$

For a high quality graphene sample (such as those prepared on SiC) the room temperature mobility can be around $10^4$ cm$^2$/(V·s)=1 m$^2$/Wb in SI units. So if we apply a field of 0.1 T we could expect to see a 1% change in the in-line conductivity, which is readily measurable.

Microwave Cavity Measurements of Off-Diagonal Conductivity

For a metal or semi-conductor enclosed within a microwave cavity, with purely diagonal conductivity tensor, the influence of the electric field vector at the conductor's surface induces current flow which is parallel to the surface electric field. The main influence on the Q factor of the enclosing cavity is to reduce it, reflecting the additional Joule heating arising from the σ·E local heating.

In the presence of a d.c. magnetic field B, the conductivity tensor takes on off-diagonal terms. This leads to a small amount of additional dissipation (remember that generally $\sigma_{xy} \ll \sigma_{xx}$) but, more importantly from the point of view of this discussion, the electric field induces a flow of current orthogonal to the other component and to itself. The orthogonal current pattern of flow over the surface acts as a radiator for the orthogonal degenerate microwave mode.

For simplicity the discussion here will be limited to resonators with cylindrical symmetry and to transverse electric (TE) modes. The graphene sample is placed on top of a single crystal sapphire puck. A TE$_{110}$ resonance is excited in the puck through a coupling port which excites the $E_r$ field. The electric field pattern of the TE$_{110}$ mode has the form of a figure of eight. For a perfectly circular puck there are two degenerate modes with relative orientations at right angles to each other.

The microwave input power port will define which of the degenerate modes is excited. An identical microwave receiver probe is placed at 180° to the input port and another identical one at 90° to it. In the absence of an applied d.c. magnetic field, the power transmitted from port 1 to port 2 shows a large Lorentzian response in the frequency domain whereas in the idealised case the port at 900 to the input port shows no output (confirming the orthogonality of the degenerate modes). Applying a d.c magnetic field changes this situation and the orthogonal current flow in the conducting sample excites the orthogonal mode so that some power will be radiated out through port 3. The ratio of the output power on resonance of port 3 (P$_3$) to port 2 (P$_2$) is capable of revealing the ratio of off-diagonal conductivity to diagonal conductivity of the conducting material for a given d.c. magnetic field and hence, substituting into the equation $$\sigma_{xy} \cong \sigma_0 \omega_c \tau = \sigma_0 \mu B$$

we are able to derive the mobility μ in a totally non-contacting method without any need for electrical contacts to the conducting film.

Experimental Method

Previously microwave cavity methods have been used to determine the Hall coefficient and hence the mobility of small semiconducting samples. The underlying process is to use a high Q copper cavity (often an ESR spectrometer is used) in which a small semiconducting sample is included. In the presence of a d.c. magnetic field the semiconducting sample excites an orthogonal mode, as described above. However the ability to characterise the Hall coefficient and mobility with any accuracy is very limited. This is mainly due to two limitations. First, only samples of very small volume can be used and usually the shape and position of the sample are critical. Calculations of the coupling between sample and cavity are problematic. Second, there is a direct effect of the magnetic field on the conducting walls of the cavity, arising from the small but finite Hall coefficient of the metal from which the cavity is made. This must be subtracted from any measured field dependence. So although the method has been used it has fallen out of favour.

Two advantages apply to the present method. First, since we are looking at graphene samples the total volume is extremely small, even though the cross-sectional area may be comparable with that of the microwave resonator. Further, the large area makes calculation and calibration simpler and more accurate. Finally we use a dielectric microwave resonator to which the graphene sample is coupled. Thus there is no first order contribution form the resonator conductivity since it is zero. Note though that there is a second order contribution from the very weak coupling between dielectric puck and the surrounding copper housing.

However carefully the sapphire puck is constructed there will inevitably be some slight non circularity which will split the degeneracy of the selected TE110 modes. Provided the split is much less than the linewidths of these modes this is not a major problem. However the degeneracy can be restored by using small tuning screws mounted in the side walls of the copper housing. By cyclic adjustment of these it is possible to ensure the degeneracy is as high as possible while also the standing wave patterns are truly orthogonal. Orthogonality is checked by connecting input and output probes to adjacent orthogonal ports (see FIG. 1) and then adjusting the screws to make the transmission a minimum on resonance.

Measurement of Mobility

Having optimised the tuning adjustment the experiment consists of making measurements of the sheet resistance of the graphene, as we have described in L Hao, J C Gallop, et al., Appl. Phys. Lett. (2013). Next the input and output are changed to orthogonal ports and the amplitude of the transmitted signal is measured as a function of an applied magnetic field.

Regarding the magnetic field dependent transmission resonances a significant result is that the orthogonal coupling power is changed by 2.4% of the peak parallel power by a d.c field of 20 mT.

$$\frac{\sigma_{xy}}{\sigma_0} = \frac{P_1}{P_2} - \mu B = 0.025$$

Thus $\mu = 0.025/0.02 = 1.25$ m$^2$/Wb = 12,500 cm$^2$/V·s for the CVD grown graphene sample, transferred to a quartz substrate. Note this is a good value for CVD graphene (see e.g. Alfonso Reina, Xiaoting Jia, John Ho, Daniel Nezich, Hyungbin Son, Vladimir Bulovic, Mildred S. Dresselhaus, and Jing Kong, Nano Lett., 2009, 9 (1), 30-35 DOI: 10.1021/nl801827v), particularly when it has been transferred to another substrate.

Calculation of Carrier Density

Having measured both the mobility and conductivity it is a straightforward step to calculate the carrier density from equation (2). Thus $$n = \frac{\sigma_0}{e\mu}$$

For our CVD sample the calculated carrier density is $7.7 \times 10^5/(1.6 \times 10^{-19} \times 1.25) = 3.8 \times 10^{24}$/m$^3$ or, more conventionally, $3.8 \times 10^{18}$/cm$^3$. To convert to the more usual 2D carrier density $\eta = nxt_g = 1.5 \times 10^{11}$/cm$^2$ where $t_g$ is the graphene film thickness, assumed to be $4 \times 10^{-8}$ cm. This is in reasonable agreement with the values measured by other techniques for similar CVD films.

Understanding the Split Mode Measurement Technique

When the housing, puck and support structure have perfect cylindrical symmetry and are exactly aligned the TE110 mode is exactly degenerate. If microwave power is injected from one port to the opposite (parallel) port the mode excited will be exactly aligned with the axis joining the two ports. The transmitted power $P_{13}$ will be given by $$P_{13}(f) = \alpha_1(\varphi_1, f)\alpha_3(\varphi_3, f)P_0$$

where $\alpha_i$ $(\varphi_i, f)$ (i=1 . . . 4) is the coupling coefficient of port i which depends on the angle $\varphi_i$ between the ith port and the primary axis of the standing wave pattern of the resonance and also on the resonant response at applied frequency f. For exact symmetry $\varphi_1 = 0$ and $\varphi_3 = \pi$. But when the exact symmetry is broken the degeneracy will be lifted too, the frequencies of the two modes will be split by an amount $\Delta f = f_u - f_l$ and the rotational symmetry is broken. Under these circumstances the ports will not couple equally to each of the split modes. The split modes will have some specific orientation related to the actual geometry of the housing so let us assume that they are orthogonal to each other but there is an angle θ between the maximum of the upper mode and the axis joining ports 1 and 3.

The frequency dependent component of the coupling constants can be assumed to follow a Lorentzian function of f, centred on the resonance frequency of the particular mode. Remember that because of the degeneracy being lifted there will be two different resonances $f_a$ and $f_b$)

$$a_i(\varphi_i, f) = \frac{L_a(f) \int \varepsilon_r \varepsilon_0 E_a^2 dv_i + L_b(f) \int \varepsilon_r \varepsilon_0 E_b^2 dv_i}{\int \varepsilon_r \varepsilon_0 E_a^2 dV + \int \varepsilon_r \varepsilon_0 E_b^2 dV}$$

The integrals in the numerator are over the volume of the ith coupling loop. $E_a$ and $E_b$ are the spatially dependent electric field distributions of the a and b modes respectively. $L_a(f)$ and $L_b(f)$ are the Lorentzian functions. In the denominator the integrals are over the entire volume of the housing, including the dielectric resonator and the substrate on which the graphene is grown.

CONCLUSIONS

We have demonstrated a novel non-contacting method for measuring both the sheet resistance (or equivalently the 2D conductivity), the mobility and carrier density of graphene at microwave frequencies. The method uses a dielectric microwave resonator and the graphene sheet is coupled to the electric field surrounding the sapphire resonator. In this way a number of restrictions previously encountered with microwave Hall effect measurements have been avoided. Data reported on a graphene sample grown by CVD on copper and then transferred to a quartz substrate is in good agreement with the numbers for similar films measured by conventional techniques involving patterning and contacting the film.

The disclosure in the abstract accompanying this application is incorporated herein by reference.

The invention claimed is:

1. A measurement device comprising:
a high permittivity dielectric resonator with a low microwave loss tangent and having at least a first symmetry axis ($z_1$);
an electrically conductive resonance chamber containing and geometrically similar to the resonator and having a second symmetry axis ($z_2$) coincident with the first symmetry axis ($z_1$);
the resonance chamber having a plurality of similar ports orthogonal to the first symmetry axis ($z_1$), each such port having a microwave antenna, either to inject microwaves into the resonance chamber, thereby to excite an electric field in the resonator, or to receive microwaves from the resonance chamber; and
a comparator circuit connected to a first one (P1) of the plurality of ports to inject microwaves into the resonance chamber and to another of the plurality of ports to receive microwaves from the resonance chamber;

wherein the measurement device also includes:

an electrically conductive tuning element in electrical contact with the resonance chamber, the tuning element being at least partially positionable in the electric field thereby excited in the resonator; and a source of magnetism to apply a magnetic field to a sample brought into proximity with a top surface of the resonator substantially parallel or anti-parallel to the first symmetry axis ($z_1$);

and wherein one of the other of the plurality of ports to receive microwaves from the resonance chamber is orthogonal to the first one of the plurality of ports to inject microwaves into the resonance chamber.

2. A measurement device according to claim 1, wherein the resonator is a right circular cylinder of rotation about the first symmetry axis ($z_1$).

3. A measurement device according to claim 1, wherein the resonator is made of a material selected from the group consisting of sapphire ($Al_2O_3$), lanthanum aluminate ($LaAlO_3$), rutile ($TiO_2$), strontium titanate ($SrTiO_3$) and magnesium oxide (MgO).

4. A measurement device according to claim 1, wherein the resonance chamber comprises an opening, allowing a sample to be introduced to a near-field region of the electric field excited in the resonator.

5. A measurement device according to claim 4, wherein the near-field region of the electric field excited in the resonator extends beyond the opening of the resonance chamber.

6. A measurement device according to claim 1, wherein the resonance chamber is made of a material selected from the group consisting of copper and aluminium.

7. A measurement device according to claim 1, wherein a second one of the other of the plurality of ports to receive microwaves from the resonance chamber is opposite the first one of the plurality of ports to inject microwaves into the resonance chamber, with the resonator located therebetween.

8. A measurement device according to claim 1, wherein a third one of the other of the plurality of ports to receive microwaves from the resonance chamber is opposite the one of the other of the plurality of ports to receive microwaves from the resonance chamber, with the resonator located therebetween.

9. A measurement device according to claim 1, wherein the tuning element is a tuning screw mounted to the resonance chamber coplanar with the plurality of ports, the tuning screw being mounted about the first symmetry axis ($z_1$) at an angle of 45 degrees to a respective one of the plurality of ports, and being at least partially positionable in the electric field of the resonator by being turnable on a screw thread.

10. A measurement device according to claim 1, wherein the microwave antenna is a straight mode or wire loop antenna.

11. A measurement device according to claim 1, wherein the relative permittivity of the resonator is greater than eight.

12. A measurement device according to claim 1, wherein the microwave loss tangent of the resonator is less than $10^{-4}$.

13. A measurement device according to claim 1, wherein the electric field excited in the resonator is a $TE_{nmp}$ mode with n >0.

14. A measurement device according to claim 1, wherein the comparator circuit comprises a vector network analyser with channels respectively connected to the first one of the plurality of ports to inject microwaves into the resonance chamber and to the other of the plurality of ports to receive microwaves from the resonance chamber.

15. A measurement device according to claim 1, wherein the comparator circuit includes a loop oscillator comprising:

a fast microwave switch connected to the other of the plurality of ports to receive microwaves from the resonance chamber;

a phase shifter connected to the fast microwave switch;

a tunable band pass filter connected to the phase shifter; and a microwave amplifier connected to the band pass filter and to the first one of the plurality of ports to inject microwaves into the resonance chamber;

the loop oscillator being connected to at least one of a counter and an oscilloscope.

16. A method of measuring the carrier mobility of a thin film, comprising:

providing a measuring device according to any preceding claim;

injecting microwaves into the resonance chamber via the first one of the plurality of ports to excite an electric field in the resonator;

receiving microwaves from the resonance chamber via the one of the other of the plurality of ports;

adjusting a position of the tuning element in the electric field thereby excited in the resonator until the microwaves received from the resonance chamber via the one of the other of the plurality of ports show that a first mode of the electric field thereby excited in the resonator is degenerate with a second mode thereof orthogonal to the first mode;

introducing a substrate having the thin film formed thereon into the near-field region of the electric field;

receiving microwaves again from the resonance chamber via the one of the other of the plurality of ports;

measuring a first peak output power of the microwaves received via the one of the other of the plurality of ports;

whilst applying a magnetic field to the substrate having the thin film formed thereon substantially parallel or anti-parallel to the first symmetry axis ($z_1$), receiving microwaves again from the resonance chamber via the one of the other of the plurality of ports;

measuring a second peak output power of the microwaves received via the one of the other of the plurality of ports; and comparing the first and second peak output powers with each other to derive the carrier mobility of the thin film.

17. A method according to claim 16, wherein the step of introducing the substrate having the thin film formed thereon into the near-field region of the electric field is conducted without contacting the resonator with either the substrate or the thin film.

18. A method according to claim 16, wherein the step of introducing the substrate having the thin film formed thereon into the near-field region of the electric field comprises the steps of:

introducing the substrate having a first thin film formed on a first side thereof and a second thin film formed on a second side thereof into the near-field region of the electric field; and contacting the second thin film with a conductor.

19. A method of measuring the conductivity or sheet resistance of a thin film, comprising:

providing a measuring device according to any one of the preceding claims;

injecting microwaves into the resonance chamber via the first one of the plurality of ports to excite an electric field in the resonator;

introducing a bare substrate into a near-field region of the electric field thereby excited in the resonator;

receiving microwaves from the resonance chamber via the second one of the other of the plurality of ports;

measuring a first resonant frequency and a first line width of the peak output power of the microwaves received via the second one of the other of the plurality of ports;

removing the bare substrate from the near-field region of the electric field excited in the resonator;

introducing a like substrate having the thin film formed thereon into the same location in the near-field region of the electric field excited in the resonator as was previously occupied by the bare substrate;

receiving microwaves from the resonance chamber via the second one of the other of the plurality of ports;

measuring a second resonant frequency and a second line width of the peak output power of the microwaves received via the second one of the other of the plurality of ports; and comparing the first and second resonant frequencies and the first and second line widths with each other to derive the conductivity or sheet resistance of the thin film.

20. A method according to claim 19, wherein the steps of introducing the bare substrate into the near-field region of the electric field excited in the resonator and introducing the like substrate having the thin film formed thereon into the same location in the near-field region of the electric field excited in the resonator are both conducted without contacting the resonator with either the substrate or the thin film.

21. A method according to claim 19, wherein the step of introducing the like substrate having the thin film formed thereon into the same location in the near-field region of the electric field excited in the resonator comprises the steps of:

introducing the like substrate having a first thin film formed on a first side thereof and a second thin film formed on a second side thereof into the same location in the near-field region of the electric field excited in the resonator; and contacting the second thin film with a conductor.

\* \* \* \* \*